United States Patent [19]
Rao

[11] Patent Number: 4,904,598
[45] Date of Patent: Feb. 27, 1990

[54] NOVEL PLASMID SHUTTLE VECTORS CONFERRING SPIRAMYCIN RESISTANCE IN STREPTOMYCES

[75] Inventor: R. Nagaraja Rao, Indianapolis, Ind.

[73] Assignee: Eli Lilly and Company, Indianapolis, Ind.

[21] Appl. No.: 841,981

[22] Filed: Mar. 20, 1986

[51] Int. Cl.$^4$ ............... C12N 1/20; C12N 15/00; C12R 1/465; C07H 21/04

[52] U.S. Cl. ............... 435/252.3; 435/172.1; 435/172.3; 435/252.32; 435/252.35; 435/320; 435/886; 536/27; 935/6; 935/9; 935/29; 935/72; 935/73; 935/75

[58] Field of Search ............... 435/68, 70, 71, 91, 435/172.1, 172.3, 253, 320, 886, 252.3, 252.31–252.35; 935/9, 14, 29, 75, 72; 536/27

[56] References Cited

U.S. PATENT DOCUMENTS 4,753,880 6/1988 Schaus et al. ............... 435/172.3

OTHER PUBLICATIONS

Pernodet et al.; Mol. Gen. Genet. 198: 35, (1984).
Manis et al., Abstracts of the Annual Meeting of American Society for Microbiology 1984, 84th Annual Meeting, St. Louis, Mo., p. 119.
Chambers and Hunter, 1984, *Biochem. Soc. Trans.*, 12:644–645.
Thompson et al., 1982, *Gene* 20:51–62.
Thompson et al., 1982, *J. Bacteriol.* 151:668–677.
Fujisawa and Weisblum, 1981, *J. Bacteriol.*, 146:621–631.
Richardson et al., (1987) *Gene* 61: 231–241.

Primary Examiner—James Martinell
Attorney, Agent, or Firm—Douglas K. Norman; Leroy Whitaker

[57] ABSTRACT

A novel gene conferring resistance to spiramycin in *Streptomyces griseofuscus* was cloned from a genomic library of *Streptomyces ambofaciens* DNA. An eighteen kb fragment of *S. ambofaciens* DNA surrounding the spiramycin resistance gene was isolated from this library on a plasmid cosmid designated pKC514. The novel spiramycin-resistance gene can be isolated on an ~3.4 kb Sau3AI fragment by subcloning restriction fragments obtained from the pKC514 insert DNA. This Sau3AI fragment contains all of the information required for the expression of the spiramycin resistant phenotype in Streptomyces. Vectors and transformants containing the novel spiramycin resistance gene are provided.

14 Claims, 7 Drawing Sheets

Restriction Site and Function Map of
Plasmid pKC514
(32.5 kb)

Restriction Site and Function Map
of Plasmid pHJL225
9.4 kb

Restriction Site and Function Map
of Plasmid pHJL401
5.8 kb

NOVEL PLASMID SHUTTLE VECTORS CONFERRING SPIRAMYCIN RESISTANCE IN STREPTOMYCES

SUMMARY OF THE INVENTION

The present invention provides spiramycin resistance-conferring shuttle vectors for use in Streptomyces. The development and exploitation of recombinant DNA technology in Streptomyces is dependent upon the availability of selectable genetic markers on suitable cloning vectors. This development has been somewhat retarded by the low number of selectable markers presently available for use in Streptomyces. The present invention is useful and especially important in that it expands the number of selectable markers suitable for such use.

The vectors of the present invention are particularly useful because they are bifunctional, versatile and can be conjugated or transformed and selected in any Streptomyces cell that is sensitive to spiramycin and permissive for the plasmid SCP2* replicon. Streptomyces provide over half of the clinically important antibiotics and thus is a commercially significant group. The present invention provides new and useful cloning vectors for this industrially important group and allows for the cloning of genes both for increasing the yields of known antibiotics, as well as for the production of new antibiotics and antibiotic derivatives.

The present invention further provides a method of selecting Streptomyces transformants from a background of untransformed cells. The method allows one to add non-selectable DNA to the present vectors, transform Streptomyces with the modified vectors and select spiramycin-resistant transformants containing this otherwise non-selectable DNA. Since transformation is a very low frequency event, such a functional test is a practical necessity for determining which cell(s), of among the millions of cells, has acquired the transforming DNA.

For purposes of the present invention, as disclosed and claimed herein, the following terms are defined below.

Recombinant DNA Cloning Vector—any autonomously replicating or integrating agent, including, but not limited to, plasmids, comprising a DNA molecule to which one or more additional DNA segments can be or have been added.

Replicon—a DNA sequence that controls and allows for autonomous replication of a plasmid or other vector.

Transformation—the introduction of DNA into a recipient host cell that changes the genotype and results in a change in the recipient cell.

Transformant—a recipient host cell that has undergone transformation.

Sensitive Host Cell—a host cell that cannot grow without a DNA segment encoding a selectable resistance characteristic.

Restriction Fragment—any linear DNA molecule generated by the action of one or more restriction enzymes.

$Am^R$—the apramycin-resistant phenotype.
$Ap^R$—the ampicillin-resistant phenotype.
cos—phage lambda cohesive end sequences. In the figures "c" denotes the left cos and "." denotes the right cos end.
$Nm^R$—the neomycin-resistant phenotype.
ori or rep—a plasmid origin of replication.
$Spi^R$—the spiramycin-resistant phenotype.
$Tc^R$—the tetracycline-resistant phenotype.
$Ts^R$—the thiostrepton-resistant phenotype.

DETAILED DESCRIPTION OF THE INVENTION

Figure 1:
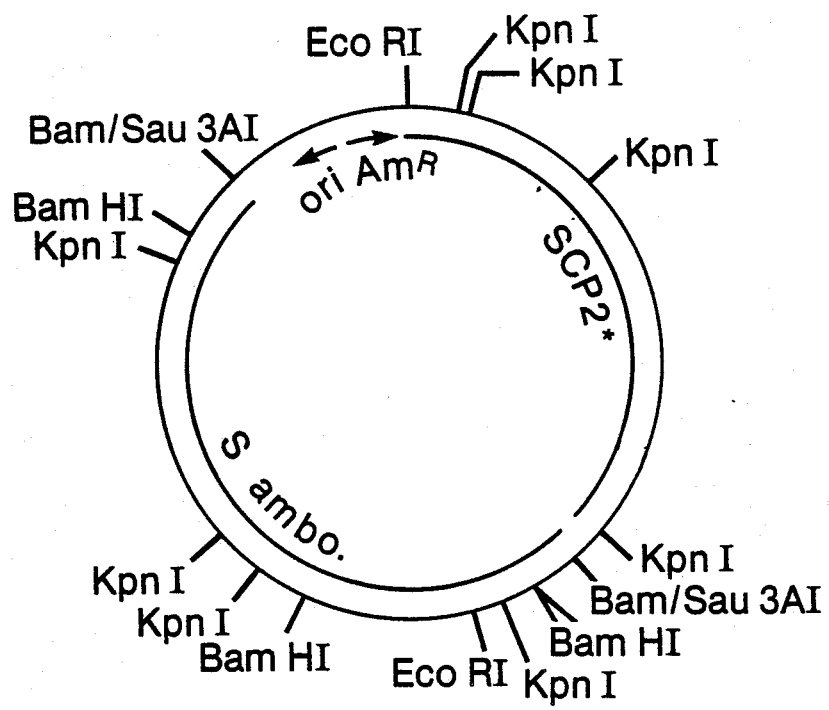
FIG. 1 shows the restriction site and function map of plasmid pKC514. For purposes of the present application, FIG. 1 and all subsequent figures are not drawn precisely to scale.

The present invention provides novel plasmid vectors comprising a DNA segment coding for a spiramycin resistance-conferring gene. These plasmids are bifunctional shuttle vectors capable of functioning in both Streptomyces and Escherichia coli. The present plasmids contain a selectable phenotype, apramycin resistance, which functions in both organisms. The plasmids further comprise a novel spiramycin resistance-conferring gene that was isolated from Streptomyces ambofaciens (NRRL 15263) and cloned into cosmid pKC505. This latter cosmid is the subject of my co-pending U.S. patent application Ser. No. 842,102 filed Mar. 20, 1986 which is expressly incorporated herein by reference.

The vectors of the present invention are Streptomyces-functional recombinant DNA expression vectors comprising a spiramycin resistance-conferring sequence of Streptomyces ambofaciens DNA that is encoded on plasmid pKC550. Two different embodiments of the present invention, designated pKC514 and pKC550, can be obtained from E. coli K12 DH1/pKC514 and E. coli JM109/pKC550, respectively, strains deposited and made part of the permanent stock culture collection of the Northern Regional Research Laboratory, Agricultural Research Service, 1815 North University Street, U.S. Department of Agriculture, Peoria, Ill. 61604. They are available to the public as a source and stock reservoir of their plasmids under the accession numbers NRRL B-18037 and B-18038 respectively.

The present vectors have been demonstrated to confer resistance to the macrolide antibiotic spiramycin. The novel spiramycin resistance gene present in these vectors may also confer resistance to other macrolide antibiotics. Such cross-resistance has been demonstrated by Fujisawa and Weisblum, J. Bacteriol. 146:621 (1981).

Varying amounts of genomic Streptomyces ambofaciens DNA were cloned into cosmid pKC505 to derive the present spiramycin resistance vectors. Eighteen kilobases (kb) of *S. ambofaciens* DNA surrounding the spiramycin resistance gene were isolated from the genomic library in a vector designated pKC514. Subcloning DNA sequences obtained from this insert DNA results in numerous derivative vectors including pKC550, described in detail herein.

The novel spiramycin resistance gene was isolated from a *Streptomyces ambofaciens* gene bank. *Streptomyces ambofaciens* is an old and well-known strain which is available to the public under the accession number NRRL B-15263. The gene bank was constructed by treating *S. ambofaciens* DNA with MboI restriction enzyme under partial digestive conditions to generate DNA fragments with an average size of 30 kb. These fragments were then subcloned into cosmid pKC505. Vector pKC505 is a bifunctional shuttle vector comprising both an *E. coli* replicon and the Streptomyces SCP2* replicon and fertility functions, three lambda cos sites and the apramycin resistance determinant which functions in both organisms. The construction of this vector is described in the examples which follow.

Figure 2:
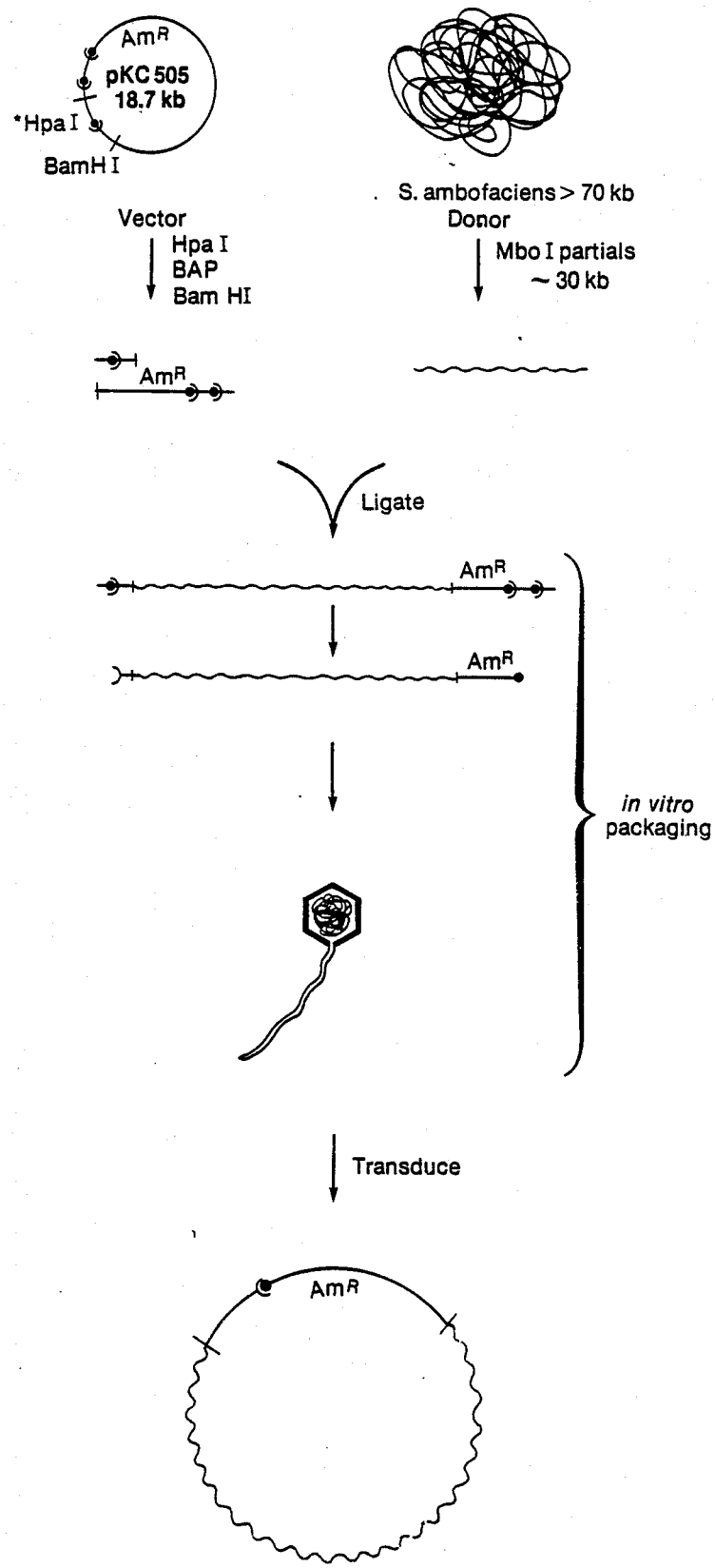
FIG. 2 is a schematic outline of the construction of genomic DNA libraries utilizing cosmid pKC505 and Streptomyces ambofaciens DNA.

Vector pKC505, isolated from *E. coli*, was treated with the restriction enzyme HpaI, generating a linear fragment with blunt ends. These HpaI ends were dephosphorylated to prevent self-ligation. The linear fragment was subsequently cut with BamHI restriction enzyme generating a small fragment with a single λ cos site and a larger fragment with two λ cos sites (see FIG. 2 of the accompanying drawings for details). Both fragments, therefore, have one dephosphorylated blunt end (non-ligatable) and another phosphorylated cohesive GATC end (ligatable to the ends generated by MboI digestion).

The DNA fragments from pKC505 and those from *Streptomyces ambofaciens* were mixed and ligated with T4 DNA ligase. After ligation, the insert DNA is flanked by the two vector fragments. Ligated DNA was packaged in vitro into bacteriophage λ particles (cosmids). The packaged cosmids were transduced into *E. coli* K12 SF8, selecting for apramycin resistance. The resulting *E. coli* transformants were pooled and used to make a primary plasmid pool. The DNA from the primary pool (library) was analyzed to make sure that the cloned library contains the desired sequences.

For functional characterization of the cloned DNA, the library was put in a suitable Streptomyces strain. Thus, the pooled plasmid DNA was used to transform *S. griseofuscus* C581 (ATCC 23916), selecting for apramycin resistance. These transformants were pooled, grown and used to select for spiramycin resistant clones.

Rapid plasmid minipreps were made from the spiramycin resistant-*S. griseofuscus* cells and the plasmid DNA was used to transform *E. coli* DH1 (NRRL B-15021) cells, selecting for apramycin resistant colonies. A number of clones were analyzed for their plasmid DNA by restriction enzyme analysis. One of the resulting plasmids was designated pKC514.

Figure 5:
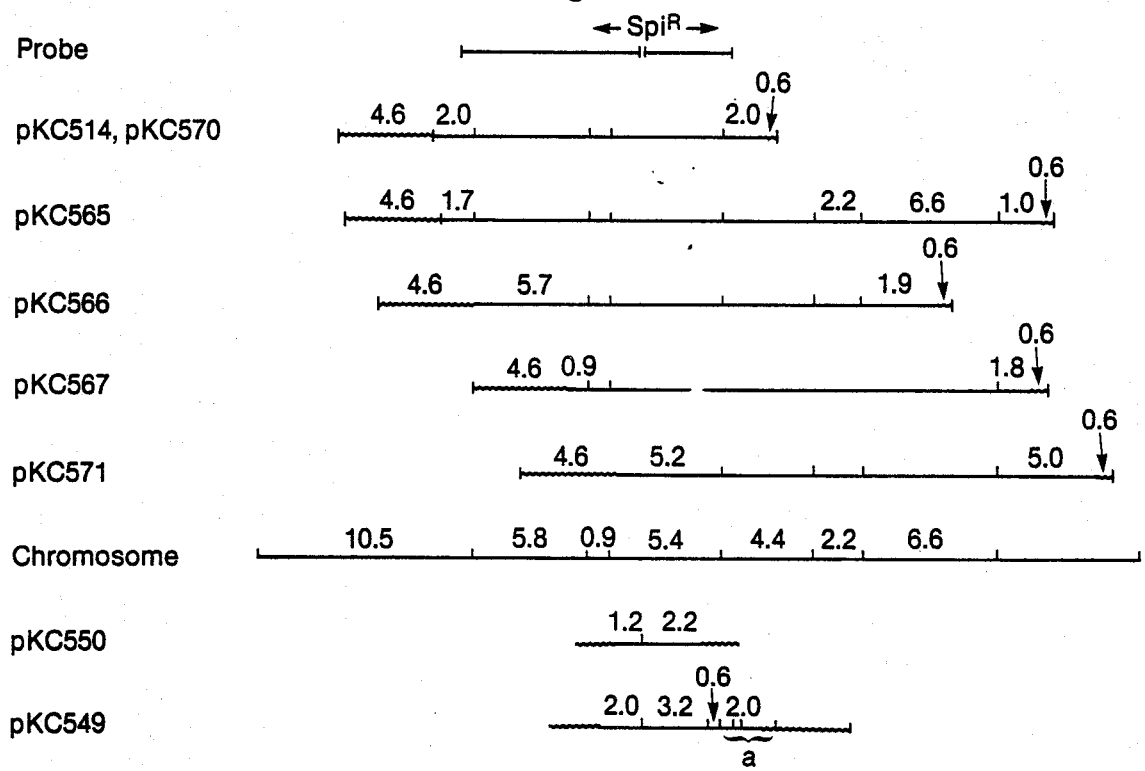
FIG. 5 shows the relationship between plasmids isolated from the primary cosmid library using probes consisting of internal BamHI fragments isolated from pKC514.

Plasmid pKC514 DNA was digested with BamHI restriction enzyme and the fragments (9.4, 4.2 kb) coming from the cloned *S. ambofaciens* DNA were used to isolate additional *E. coli* colonies from the primary library. One of these clones contained a plasmid designated pKC570, whose structure was very similar to that of pKC514. FIG. 5 illustrates the relationship between these *E. coli* clones. The aforementioned BamHI fragments (designated on the first line shown in FIG. 5) were isolated from pKC514 and used to probe the library. Vectors pKC565, pKC566, pKC567, pKC570 and pKC571 were isolated from this probing experiment. All of these vectors, except for pKC571, when transferred to *Streptomyces griseofuscus*, conferred spiramycin resistance. KpnI restriction sites are indicated in the figures.

FIG. 5 further illustrates vectors derived from the subcloning experiments described herein. For example, plasmid pKC550 was isolated by subcloning Sau3AI partial fragments from the cloned insert DNA into plasmid pHJL401, a plasmid disclosed in U.S. Ser. No. 841,920, filed Mar. 20, 1986 by Hershberger, Larson, and Reynolds, with selection for a spiramycin resistant phenotype. The site indicated in the pKC550 fragment is a BamHI site (see FIG. 4 for details). Plasmid pKC549 was isolated by subcloning SalI partial fragments in pHJL401 and selecting for a spiramycin resistant phenotype. The sites indicated in the pKC549 fragment are BamHI, EcoRI, KpnI, BamHI, BamHI, and KpnI, respectively. Most of the distances between the restriction sites are represented on the drawing. Moreover, the distance between the two KpnI sites designated "a" in FIG. 5 is 2.0 kb; the distance between the two internal BamHI sites has not been analyzed.

The spiramycin resistance conferring restriction fragment is not limited to a particular vector or a position on a cloning vector, as long as the critical vector-controlled functions are not disrupted. For example, the spiramycin resistance gene can be subcloned into other known vectors such as the pSCP103-derived plasmids (Lydiate et al., 1985, *Gene* 35:223), the pFJ103-derived plasmids (Richardson et al., 1982, Gene 20:451), and pHJL401 (Hershberger et al. 1986). Those skilled in the art understand or can readily determine which vector is desirable for a specific purpose and which sites on a vector are advantageous for the ligation or insertion of a particular spiramycin resistance gene-containing restriction fragment.

Plasmid pKC514, useful directly as a cloning vector, can also be used to construct derivative vectors, such as plasmids pKC549 and pKC550, that fall within the scope of the present invention. In addition, to these specific vectors, derivative vectors can be constructed by providing molecular linkers to a particular spiramycin resistance gene-containing restriction fragment thereby creating specific sites for DNA subcloning. Furthermore, the various spiramycin resistance gene-containing restriction fragments can be modified by adding, eliminating, or substituting certain nucleotides to alter characteristics and to provide a variety of restriction sites for ligation of DNA. Those skilled in the art understand nucleotide chemistry and the genetic code and thus which DNA modifications are desirable for a specific purpose.

Figure 4:
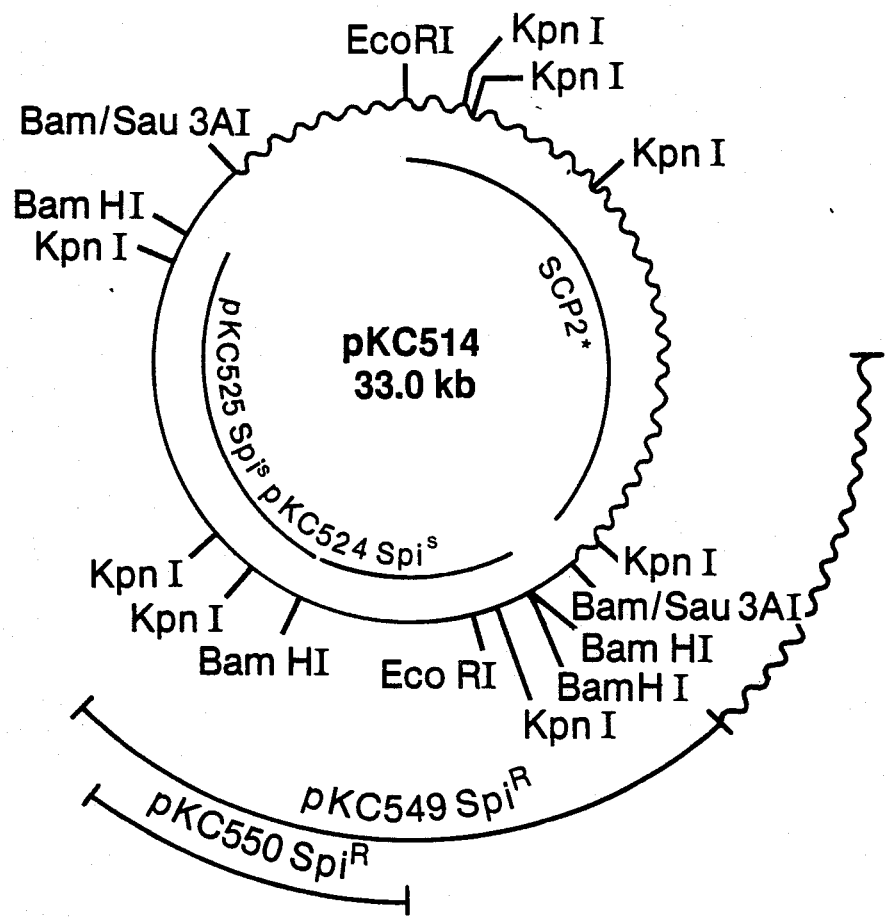
FIG. 4 shows the relationship between the different subcloned fragments of Streptomyces ambofaciens DNA and plasmid pKC514.

*Streptomyces ambofaciens* DNA in plasmid pKC514 was subcloned into pHJL401 as detailed in FIG. 4. The wavy line represents vector pKC505 DNA and the straight line represents the insert DNA from *S. ambofaciens* chromosome. All of the subloning was performed in pHJL401. Plasmid pKC550 has an approximate insert size of 3.4 kb and pKC549 has an approximate insert size of 11.0 kb. Both plasmids confer Spi$^R$ phenotype to *S. griseofuscus* transformants. The subcloning of pKC514 BamHI insert fragments into pHJL401 generated pKC524 (10.7 kb) and pKC525 (15.7 kb). However, neither of these plasmids conferred Spi$^R$ phenotype to *S. griseofuscus* transformants. The relationship between the subcloned DNA to the original vector pKC514 is illustrated in FIG. 4 of the accompanying drawings.

Although the above-described vectors comprise the SCP2* Streptomyces replicon derived from cosmid pKC505, a variety of known Streptomyces replicons can be used to construct similar vectors. Table 1 is an illustrative, but not comprehensive, listing of Streptomyces plasmids from which additional, functional Streptomyces replicons can be obtained. Those skilled in the art recognize that all or part of the plasmids may be used to construct vectors exemplifying the present invention so long as the replicon function is not disrupted. The plasmid-containing host and depository accession number are also listed in Table 1.

TABLE 1
Streptomyces Plasmids

| Plasmid | Host | Accession Number |
| --- | --- | --- |
| SCP2 | Streptomyces coelicolor A3(2) | NRRL 15042 |
| pEL7 | Streptomyces ambofaciens | |
| pEL7 | NRRL 12523 | |
| pUC6 | Streptomyces espinosus | NRRL 11439 |
| pUC3 | Streptomyces 3022A | NRRL 11441 |
| SLP1 | Streptomyces lividans | NCIB[1] 11417 |
| pNM100 | Streptomyces virginiae | NRRL 15156 |
| pEL103 | Streptomyces granuloruber A39912.13/pEL103 | NRRL 12549 |
| pIJ702 | Streptomyces lividans | ATCC[2] 39155 |

[1]National Collection of Industrial Bacteria (NCIB), Torry Research Station, Post Office Box 31, 135 Abbey Road, Aberdeen AB98DG, Scotland, United Kingdom
[2]American Type Culture Collection (ATCC), 12301 Parklawn Drive, Rockville, Maryland 20852, United States of America The vectors of the present invention comprise a Streptomyces replicon, an *E. Coli* replicon, and a spiramycin resistance-conferring restriction fragment. Because amplification and manipulation of plasmids is done faster and more efficiently in *E. coli* than in Streptomyces, the presence of an *E. coli* replicon is advantageous and adds to the general utility of the present illustrative vectors. Since the presence of a particular *E. coli* replicon is not a critical component of the present vectors, the substitution of functional replicon-containing and, if desired, antibiotic resistance-conferring restriction fragments from *E. coli* plasmids such as, for example, pCZ101 (Schoner et al., 1984, *Proc. Natl. Acad. Sci. USA* 81:5403), pACYC184, pBR325, pBR328 and the like is within the scope of the present invention.

The wealth of genetic and biochemical information about *E. coli* makes it a convenient host cell for purposes of the present invention. However, the invention is not limited to any one genus, species, or strain but can be used with any organism where the *E. coli* replicon is functional. A number of possible host cells are exemplified throughout the specification and examples.

The vectors used in the present method confer spiramycin resistance to spiramycin-sensitive Streptomyces or related host cells. Although 25 μg/ml of spiramycin is generally toxic to spiramycin-sensitive Streptomyces, vectors of the present invention confer resistance to levels approaching 100 μg/ml of spiramycin. The preferred spiramycin concentration for purposes of selection for other Streptomyces species is readily determined by procedures well-known in the art. While all embodiments of the present invention are useful, some of the vectors and transformants are preferred. Accordingly, preferred vectors and transformants are listed in Table 2.

TABLE 2

| Preferred Transformants | |
| --- | --- |
| Vector | Transformant |
| pKC514 | Streptomyces griseofuscus |
| pKC549 | Streptomyces griseofuscus |
| pKC550 | Streptomyces griseofuscus |
| pKC565 | Streptomyces griseofuscus |
| pKC566 | Streptomyces griseofuscus |
| pKC567 | Streptomyces griseofuscus |
| pKC570 | Streptomyces griseofuscus |

The recombinant DNA cloning vectors of the present invention are not limited for use in a single species or strain of Streptomyces. To the contrary, the vectors are broadly applicable and can be used with spiramycin-sensitive host cells of many Streptomyces taxa, particularly restrictionless strains of economically important taxa that product antibiotics such as aminoglycoside, macrolide, β-lactam, polyether and glycopeptide antibiotics. Such restrictionless strains are readily selected and isolated from Streptomyces taxa by conventional procedures well-known in the art (Lomovskaya et al., 1980, *Microbiological Reviews* 44:206). Host cells of restrictionless strains lack restriction enzymes and, therefore, do not cut or degrade plasmid DNA upon transformation. For purposes of the present application, host cells containing restriction enzymes that do not cut any of the restriction sites of the present vectors are also considered restrictionless.

Preferred host cells of restrictionless strains of spiramycin-sensitive Streptomyces taxa that produce aminoglycoside antibiotics, and in which the present vectors may be transformed, include restrictionless cells of, for example: *Streptomyces kanamyceticus* (kanamycins), *S. chrestomyceticus* (aminosidine), *S. griseoflavus* (antibiotic MA 1267), *S. microsporeus* (antibiotic SF-767), *S. ribosidificus* (antibiotic SF733), *S. flavopersicus* (spectinomycin), *S. spectabilis* (actinospectacin), *S. rimosus* forma *paromomycinus* (paromomycins, catenulin), *S. fradiae* var. *italicus* (aminosidine), *S. bluensis* var. *bluensis* (bluensomycin), *S. catenulae* (catenulin), *S. olivoreticuli* var. *cellulophilus* (destomycin A), *S. lavendulae* (neomycin), *S. alboqriseolus* (neomycins), *S. tenebrarius* (tobramycin, apramycin), *S. albus* var. *metamycinus* (metamycin), *S. hygroscopicus* var. *sagamiensis* (spectinomycin), *S. bikiniensis* (streptomycin), *S. griseus* (streptomycin), *S. erythrochromogenes* var. *narutoensis* (streptomycin), *S. poolensis* (streptomycin), *S. galbus* (streptomycin), *S. rameus* (streptomycin), *S. olivaceus* (streptomycin), *S. mashuensis* (streptomycin), *S. hygroscopicus* var. *limoneus* (validamycins), *S. rimofaciens* (destomycins), *S. hygroscopicus* forma *glebosus* (glebomycin), *S. fradiae* (hybrimycins neomycins), *S. eurocidicus* (antibiotic A16316-C), *S. aquacanus* (N-methyl hygromycin B), *S. crystallinus* (hygromycin A), *S. noboritoensis* (hygromycin), *S. hygroscopicus* (hygromycins), *S. atrofaciens* (hygromycin), *S. kasugaspinus* (kasugamycins), *S. kasugaensis* (kasugamycins), *S. netropsis* (antibiotic LL-AM31), *S. lividus* (lividomycins), *S. hofuensis* (seldomycin complex) and *S. canus* (ribosyl paromamine).

Preferred host cells of restrictionless strains of spiramycin-sensitive Streptomyces taxa that produce macrolide antibiotics, and in which the present vectors may be transformed, include restrictionless cells of, for example: *Streptomyces caelestis* (antibiotic M188), *S. platensis* (platenomycin), *S. rochei* var. *volubilis* (antibiotic T2636), *S. venezuelae* (methymycins), *S. griseofuscus*

(bundlin), *S. narbonensis* (josamycin, narbomycin), *S. fungicidicus* (antibiotic NA-181), *S. griseofaciens* (antibiotic PA133A, B), *S. roseocitreus* (albocycline), *S. bruneogriseus* (albocycline), *S. roseochromogenes* (albocycline), *S. cinerochromogenes* (cineromycin B), *S. albus* (albomycetin), *S. felleus* (argomycin, picromycin), *S. rochei* (lankacidin, borrelidin), *S. violaceoniger* (lankacidin), *S. griseus* (borrelidin), *S. maizeus* (ingramycin), *S. albus* var. *coilmyceticus* (coleimycin), *S. mycarofaciens* (acetyl-leukomycin, espinomycin), *S. griseospiralis* (relomycin), *S. lavendulae* (aldgamycin), *S. rimosus* (neutramycin), *S. deltae* (deltamycins), *S. fungicidicus* var. *espinomyceticus* (espinomycins), *S. furdicidicus* (mydecamycin), *S. eurocidicus* (methymycin), *S. griseolus* (griseomycin), *S. flavochromogenes* (amaromycin, shincomycins), *S. fimbriatus* (amaromycin), *S. fasciculus* (amaromycin), *S. erythreus* (erythromycins), *S. antibioticus* (oleandomycin), *S. olivochromogenes* (oleandomycin), *S. spinichromogenes* var. *suragaoensis* (kujimycins), *S. kitasatoensis* (leucomycin), *S. narbonensis* var. *josamyceticus* (leucomycin A3, josamycin), *S. albogriseolus* (mikonomycin), *S. bikiniensis* (chalcomycin), *S. cirratus* (cirramycin), *S. djakartensis* (niddamycin), *S. eurythermus* (angolamycin), *S. goshikiensis* (bandamycin), *S. griseoflavus* (acumycin), *S. halstedii* (carbomycin), *S. tendae* (carbomycin), *S. macrosporeus* (carbomycin), *S. thermotolerans* (carbomycin), and *S. albireticuli* (carbomycin).

Preferred host cells of restrictionless strains of spiramycin-sensitive Streptomyces taxa that produce β-lactam antibiotics, and in which the present vectors may be transformed, include restrictionless cells of, for example: *Streptomyces lipmanii* (A16884, MM4550, MM13902), *S. clavuligerus* (A16886B, clavulanic acid), *S. lactamdurans* (cephamycin C), *S. griseus* (cephamycin A, B), *S. hygroscopicus* (deacetoxycephalosporin C), *S. wadayamensis* (WS-3442-D), *S. chartreusis* (SF 1623), *S. heteromorphus* and *S. panayensis* (C2081X); *S. cinnamonensis, S. fimbriatus, S. halstedii, S. rochei* and *S. viridochromogens* (cephamycins A, B); *S. cattleya* (thienamycin); and *S. olivaceus, S. flavovirens, S. flavus, S. fulvoviridis, S. argenteolus* and *S. sioyaensis* (MM 4550 and MM 13902).

Preferred host cells of restrictionless strains of spiramycin-sensitive Streptomyces taxa that produce polyether antibiotics, and in which the present vectors may be transformed, include restrictionless cells of, for example: *Streptomyces albus* (A204, A28695A and B, salinomycin), *S. hygroscopicus* (A218, emericid, DE3936), A120A, A28695A and B, etheromycin, dianemycin), *S. griseus* (grisorixin), *S. conglobatus* (ionomycin), *S. eurocidicus* var. *asterocidicus* (laidlomycin), *S. lasaliensis* (lasalocid), *S. ribosidificus* (lonomycin), *S. cacaoi* var. *asoensis* (lysocellin), *S. cinnamonensis* (monensin), *S. aureofaciens* (narasin), *S. gallinarius* (RP 30504), *S. longwoodensis* (lysocellin), *S. flaveolus* (CP38936), *S. mutabilis* (S-11743a) and *S. violaceoniger* (nigericin).

Preferred host cells of restrictionless strains of spiramycin-sensitive Streptomyces taxa or related genera such as, for example, Nocardia that produce glycopeptide antibiotics, and in which the present vectors may be transformed, include restrictionless cells of, for example: *Nocardia orientalis* and *Streptomyces haranomachiensis* (vancomycin); *Nocardia candidus* (A-35512, avoparcin), *S. eburosporeus* (LL-AM 374), *S. virginiae* (A41030) and *S. toyocaensis* (A47934).

Preferred host cells of restrictionless strains of spiramycin-sensitive Streptomyces taxa, and in which the present vectors may be transformed, include restrictionless cells of, for example: *Streptomyces coelicolor, S. granuloruber, S. roseosporus, S. acrimycins, S. qlaucescens, S. parvilin, S. pristinaespiralis, S. violaceoruber, S. vinaceus, S. espinosus, S. azureus, S. griseofuscus, S. fradiae* and *S. toyocaensis.*

The recombinant DNA vectors of the present invention have broad utility and help fill the need for suitable cloning vehicles for use in Streptomyces and related organisms. More particularly, the present vectors are used as a means for selecting a recombinant DNA-containing Streptomyces host cell. This is accomplished by transforming a spiramycin-sensitive, preferably restrictionless Streptomyces host cell with one of the present vectors, such as pKC514, and culturing the transformed cell under conditions suitable for selection for spiramycin resistance. Moreover, the ability of the present vectors to confer spiramycin resistance provides a functional means for selecting transformants. This is important because of the practical necessity for determining and selecting the particular cells that have acquired vector DNA.

Additional DNA segments, that lack functional tests for their presence, can also be inserted onto the present vectors and then transformants containing the non-selectable DNA can be isolated by spiramycin selection. Such non-selectable DNA segments can be inserted at any site, except within regions necessary for plasmid function and replication or within the spiramycin resistance-conferring gene, and include, but are not limited to, genes that specify antibiotic modification enzymes and regulatory genes of all types.

The spiramycin resistance-conferring vectors of the present invention are also useful for ensuring that linked DNA segments are stably maintained in host cells over many generations. These genes or DNA fragments, covalently linked to the spiramycin resistance-conferring restriction fragment and propagated in Streptomyces, are maintained by exposing the transformants to levels of spiramycin that are toxic to non-transformed cells. Therefore, transformants that lose the vector, and consequently any covalently linked DNA, cannot grow and are eliminated from the culture. Thus, the vectors of the present invention can stabilize and maintain any DNA sequence of interest.

The method, vectors and transformants of the present invention provide for the cloning of genes to improve yields of various products that are currently produced in Streptomyces and related cells. Examples of such products include, but are not limited to, Streptomycin, Cephalosporins, Actaplanin, Apramycin, Narasin, Monensin, Tobramycin, Erythromycin and the like. The present invention also provides selectable vectors that are useful for cloning, characterizing and reconstructing DNA sequences that code for commercially important proteins such as, for example, human insulin, human proinsulin, glucagon, interferon and the like; for enzymatic functions in metabolic pathways leading to commercially important processes and compounds; or for control elements that improve gene expression. These desired DNA sequences also include, but are not limited to, DNA that codes for enzymes that catalyze synthesis of derivatized antibiotics such as, for example, Streptomycin, Cephalosporin, Apramycin, Actaplanin, Narasin, Tobramycin, Monensin and Erythromycin derivatives, or for enzymes that mediate and increase bioproduction of antibiotics or other products. The capability for inserting and stabilizing such DNA segments thus allows for increasing the yield and availability of antibiotics that are produced by Streptomyces and related organisms.

Streptomyces can be cultured in a number of ways using any of several different media. Carbohydrate sources which are preferred in a culture medium include, for example, molasses, glucose, dextrin and glycerol. Nitrogen sources include, for example, soy flour, amino acid mixtures and peptones. Nutrient inorganic salts are also incorporated and include the customary salts capable of yielding sodium, potassium, ammonium, calcium, phosphate, chloride, sulfate and like ions. As is necessary for the growth and development of other microorganisms, essential trace elements are also added. Such trace elements are commonly supplied as impurities incidental to the addition of other constituents of the medium. Specific culture media are disclosed in the examples.

Streptomyces is grown under aerobic culture conditions over a relatively wide pH range of about 5 to 9 at temperatures ranging from about 15° to 40° C. For plasmid stability and maintenance, it is desirable to start with a culture medium at a pH of about 7.2 and maintain a culture temperature of about 30° C.

Escherichia coli K12 strains can also be cultured in a number of ways using any of several different media. Carbohydrate sources which are preferred in a culture medium include glucose and glycerol; nitrogen sources include ammonium salts, amino acid mixtures, and peptones. Nutrient inorganic salts are also incorporated and include those listed for Streptomyces, as well as salts yielding magnesium ions.

E. coli can be grown under aerobic culture conditions over a pH range of 6.5 to 7.5 at temperatures ranging from about 25° to 42° C. For plasmid stability maintenance, it is desirable to start with a culture medium at a pH of about 7.2 and maintain a culture temperature of about 30° C.

EXAMPLE 1

Culture of E. coli K12 DH1/pKC420 and Isolation of Cosmid pKC420

A. Culture

Five ml cultures of E. coli K12 DH1/pKC420 (NRRL B-15837) were grown under selective conditions in TY media (1tryptone 0.5% yeast extract, 0.5% sodium chloride pH 7.4) according to conventional microbiological procedures. The cells were spun in a table top centrifuge and the pellet resuspended in 1 ml of 0.3 M sucrose, 25 mM EDTA (ethylenediaminetetraacetate) and 25 mM Tris-HCl pH 8 (Solution I). After transfer to an Eppendorf tube the cells were centrifuged for about one minute and the pellet was resuspended in 0.5 ml of Solution I. About 50 $\mu$l of freshly made lysozyme (20 mg/ml in water) were added and the solution was incubated for 10 minutes at 37° C.

After the addition of 250 $\mu$l of freshly made lysis mix (2sodium dodecyl sulfate and 0.3 N NaOH), the cells were immediately and completely vortexed. The cells were then incubated for ten minutes at 50° C., cooled and 100 $\mu$l of phenol-Sevag (phenol-chloroform-isoamyl alcohol, 25-24-1) was added. The tube was vortexed for one minute. The DNA was centrifuged for two minutes in an Eppendorf centrifuge, the supernatant was pipetted and transferred to another tube with 70 $\mu$l of unbuffered 3 M sodium acetate and 0.7 ml of isopropanol to precipitate the DNA. This solution was incubated for five minutes at room temperature and then centrifuged for two minutes. The supernatant was gently and completely decanted to remove all the excess liquid.

The DNA precipitate was redissolved in 500 $\mu$l of TE (10 mM Tris-HCl pH8 and 1 mM EDTA) and 10 $\mu$l of 100 mM Spermine HCl were added. This mixture was vortexed and then incubated for five minutes at room temperature before a five minute spin in an Eppendorf centrifuge. The supernatant was again completely decanted and discarded and the precipitated DNA was vortexed with 1 ml of 75% ethanol, 0.3 M sodium acetate, and 10 mM magnesium acetate. This solution was incubated for five minutes at room temperature and the DNA collected as above. The pellet was redissolved in 10 $\mu$l of TE for subsequent use as a cloning vehicle.

EXAMPLE 2

Construction of Plasmid pHJL202

The plasmid pHJL202 contains the streptomycetes replicon from plasmid SCP2* (Bibb et al., 1977, *Molec. Gen. Genet.* 154:155), as well as neomycin resistance and ampicillin resistance genes. The construction of pHJL202 is disclosed below.

A. Partial KpnI Digestion of Plasmid pJL192

About 13 $\mu$l (~3.25 $\mu$g) of plasmid pJL192 DNA, isolated from E. coli K12 C600R$_K$-M$_K$-/pJL192 (NRRL B-15040) and prepared according to the teaching of Example 1, 25 $\mu$l water, 5 $\mu$l BSA, 5 $\mu$l 10X KpnI restriction buffer and 2 $\mu$l KpnI enzyme* were mixed and incubated at 37° C. for 45 minutes. A ten $\mu$l aliquot was removed, mixed with 40 $\mu$l water and heated at 70° C. for 10 minutes to inactivate the enzyme. This protocol produces all possible reaction products ranging from molecules that have not been cleaved by the KpnI restriction enzyme to those that have been completely digested by the KpnI restriction enzyme. The aliquot was precipitated with 1/10 volume 3M NaOAc pH 8 and 2 volumes ethanol and then frozen at $-70$° C. for 1 hour.

B. Ligation

The precipitate was collected, washed twice, air dried and then resuspended in 20 $\mu$l water. About 6 $\mu$l of the reaction was removed and mixed with a solution of 20 $\mu$l 5X kinase/ligase buffer (250 mM Tris-HCl pH 7.8, 5Glycerol, 25 mM Dithiothreitol, and 50 mM MgCl$_2$) 40 $\mu$l 0.66 M ATP pH 7.4, 33 $\mu$l water and 1 $\mu$l T4 DNA ligase and incubated at 15° C. for 72 hours to promote self-circularization. After incubation, 50 $\mu$l were removed from the reaction and the reaction was terminated by increasing the temperature at 70° C. for 10 minutes. The reaction products were precipitated as above and resuspended in 15 $\mu$l water.

*Restriction and other enzymes can be readily obtained from the following sources:
New England Biolabs., Inc., 32 Tozer Road, Beverly, Mass. 01915
Bethesda Research Laboratories, Inc., P.O. Box 577, Gaithersburg, Md. 20760
Boehringer Mannheim Biochemicals, P.O. Box 50816, Indianapolis, Ind. 46250

C. Transformation

Frozen, competent E. coli K12 C600R$_K$-M$_K$- cells thawed in an ice bath and mixed in a ratio of 0.1 ml of cells to 0.05 ml of plasmid DNA and 37.5 $\mu$l of 0.1X SSC (0.015M NaCl, 0.0015M Sodium Citrate at pH 7).

The transformation mixture was chilled on ice for 20 minutes, heat shocked at 42° C. for 1 minute and chilled on ice for 10 minutes. The samples were then diluted with 0.85 ml of L-broth, incubated at 37° C. for 1.5 hours, spread on L-agar containing ampicillin (50 μg/ml) and incubated for 18 hours at 37° C. The resulting colonies of correct phenotype, ampicillin resistant ($Ap^R$) and tetracycline sensitive ($Tc^S$) were screened for plasmid size in substantial accordance with the method of in-the-well-lysis as described by Eckhardt et al., 1978, *Plasmid* 1:584 (1978). The ampicillin resistant and tetracycline sensitive colonies containing the desired ~18 kb plasmid were isolated according to known procedures, cultured, and used to purify covalently closed circular DNA which was then conventionally identified by restriction enzyme and agarose gel electrophoretic (AGE) analysis of the constitutive plasmids. The identified *E. coli* K12 $C600R_K$-$M_K$-/pHJL202 transformants were then used for subsequent production and isolation of plasmid pHJL202 according to the teaching of Example 1 except that strains containing the desired pHJL202 plasmid were used instead of *E. coli* K12 DH1/pKC420.

EXAMPLE 3

Construction of Cosmid pKC473

To obtain the cosmid backbone used in the construction of cosmid pKC473, pKC420 DNA can be conventionally treated with EcoRI and BamHI restriction enzymes in accordance with the conditions recommended by the enzyme manufacturer. The resulting fragments can then be ligated to a gel-purified ~375 bp EcoRI-BamHI restriction fragment from plasmid pBR322 which contains a portion of the tetracycline resistance gene. The ligation products are used to transform *E. coli* in substantial accordance with the teaching of Example 2C and transformants having ampicillin and tetracycline resistant, apramycin sensitive phenotypes are selected. These transformants can then be conventionally cultured for subsequent production and isolation of their cosmid DNA.

Next, the ~752 bp EcoRI-PstI fragment containing a portion of the ampicillin resistance gene present in the above-constructed intermediate cosmid was deleted. The apramycin resistance ($Am^R$) gene from plasmid pKC222 (Rao et al., 1983, *Antimicrobial Agents and Chemotherapy* 24(5):689) was subcloned into the deleted EcoRI-PstI region of the intermediate cosmid on an ~1500 bp EcoRI-PstI fragment. The ligated material was used to transform *E. coli* K12 DH1. The identity of the desired transformants was conventionally confirmed by initially selecting for $Tc^R$ phenotype and then replicating those $Tc^R$ colonies to select for $Am^R$ colonies. The resultant *E. coli* K12 DH1/pKC473 transformants were conventionally cultured for subsequent production and isolation of cosmid pKC473.

EXAMPLE 4

Construction of Cosmid Shuttle Vector pKC505

Figure 3:
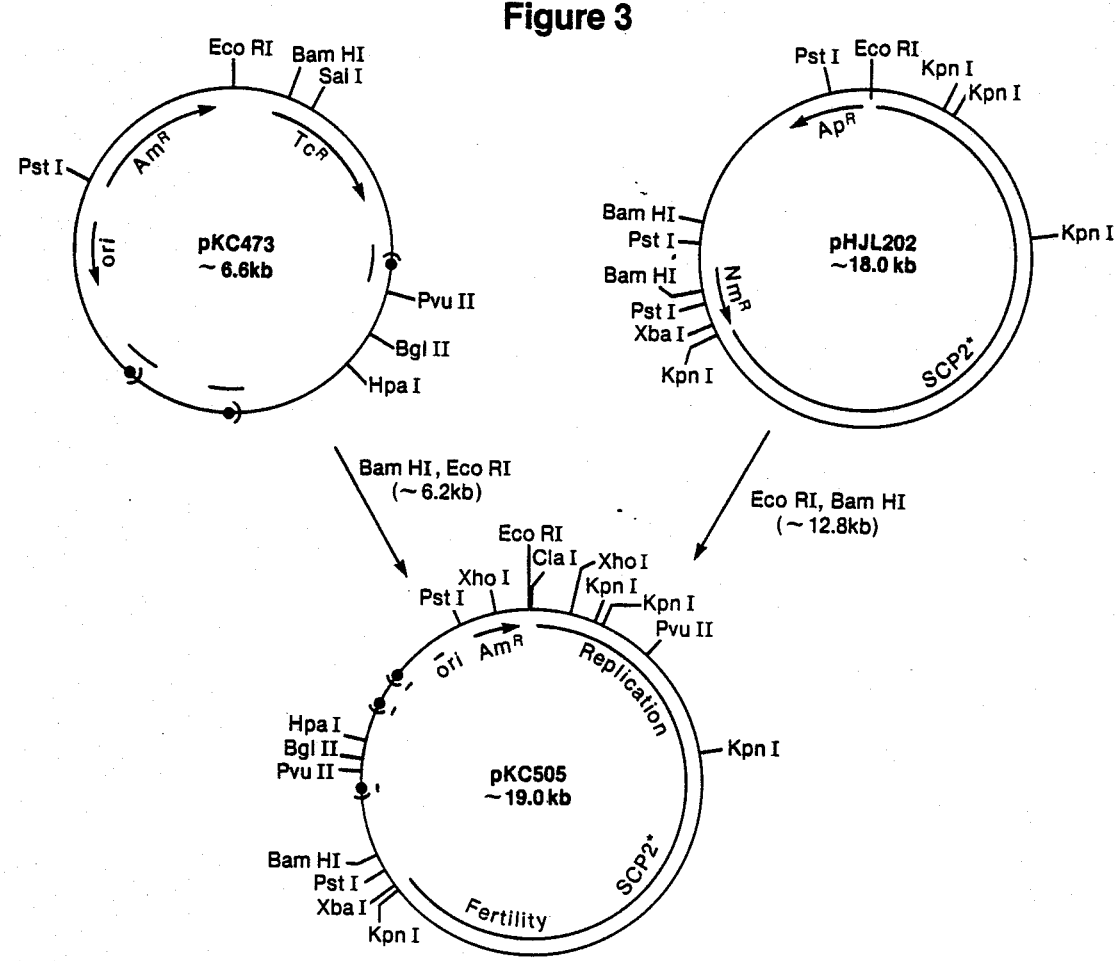
FIG. 3 is a flow chart illustrating the construction of cosmid pKC505.

Cosmid pKC505 was constructed from DNA restriction fragments of cosmid pKC473 and plasmid pHJL202 using conventional and well understood techniques for restriction enzyme digestion and ligation. The construction of cosmid pKC505 is illustrated by flow chart in FIG. 3 of the accompanying drawings. Generally, the two vectors, pKC473 and pHJL202, were individually treated in a double digest reaction with BamHI and EcoRI restriction enzymes to generate linear fragments. These digestion products were mixed and the fragments ligated and used to transform *Streptomyces ambofaciens* selecting for apramycin resistance. The resulting plasmid, designated pKC505, comprises the pKC473 vector backbone and an ~12.8 kb BamHI-EcoRI fragment encoding the SCP2* replication and fertility 30 functions from plasmid pHJL202. This ~12.8 kb fragment replaced the ~375 bp fragment coding for the $Tc^R$ gene of pKC473.

Cosmid pKC505 was subsequently shuttled into *E. coli* to verify the structure of the cosmid by restriction enzyme analysis. Cosmid pKC505 was back-transformed into *Streptomyces ambofaciens* to check its ability to function as a shuttle vector.

Example 5

Construction of *Streptomyces ambofaciens*/pKC505

About 1 μg of the DNA from Example 4 and 200 μl of protoplasts of *Streptomyces ambofaciens* (NRRL 263) were mixed with 500 μl of 55% polyethylene glycol (Sigma) in P medium (Hopwood and Wright, 1978, *Molecular and General Genetics* 162:307), vortexed, and then aliquots of 25 μl and 250 μl were plated onto R2YE* plates with 3 ml of R2YE top agar. The plates were incubated for 18 hours at 30° C. and then overlayed with 3 ml of R2YE top agar containing sufficient apramycin** for a final concentration of 50 μg/ml. The plates were then incubated for an additional 3 days at 30° C. The identity of the desired transformants was conventionally confirmed by selecting for apramycin resistance. The resulting *S. ambofaciens*/pKC505 apramycin resistant colonies were isolated according to known procedures, cultured and used for production of cosmid pKC505 DNA. Cosmid pKC505 DNA was transformed into *E. coli* for characterization and verification.

| Sucrose | 103 g | Trace Element Mix | 2 ml |
|---|---|---|---|
| 2.5% $K_2SO_4$ | 10 ml | 0.5% $KH_2PO_4$ | 10 ml |
| $MgCl_2$ | 10.1 g | 1M $CaCl_2$ | 20 ml |
| Glucose | 10 g | Proline | 3 g |
| Casamino acids | 0.1 g | 0.25 M TES pH 7.2 | 100 ml |
| Agar | 22 g | 10% Yeast Extract | 50 ml |

**Antibiotic apramycin can be obtained from either Sigma, St. Louis, Mo. or Eli Lilly and Company, Indianapolis, Ind.

EXAMPLE 6

The Construction of a Genomic Library

A. Preparation of the Vector pKC505 DNA

About 50 μg of vector pKC505 DNA was digested with 50 units of HpaI in a 100 μl reaction at 37° C. for one hour. Complete digestion produced one band migrating at 18.7 kb on a 0.3% agarose gel. The DNA was extracted with an equal volume of phenol saturated with TE, then with Sevag and precipitated with ethanol (three volumes). After 10 minutes of centrifugation in an Eppendorf centrifuge, the DNA was redissolved in 100 μl of water, to which 20 μl of 10X BAP buffer (0.5 M Tris-HCl pH 8.0, 0.5 M NaCl) and 80 μl of bacterial alkaline phosphatase (BAP, 24 μ/ml) were added. Dephosphorylation was done for one hour at 70° C. The DNA was extracted and precipitated as before and dissolved in 50 μl of 5 mM NaCl. The DNA was then digested with 50 units of BamHI in a 100 μl reaction at 37° C. for two hours. Complete digestion produces two bands at 16.7 kb and 2.0 kb. The DNA was again extracted with phenol, Sevag, precipitated with ethanol and dissolved in 50 μl of TE. About 0.5 μg of DNA can be used in a ligase reaction to check the ligatability of the BamHI ends. Ligation produces 3 bands at 33.4 kb, 18.7 kb, and 4.0 kb.

B. Preparation of the Insert DNA

About 2.5 ml of fresh overnight culture of *Streptomyces ambofaciens* was used to inoculate 50 ml of TSB. The culture was grown overnight at 30°–32° C. with vigorous shaking. The cells were harvested by centrifugation, suspended in 10 ml lysis buffer (15% Sucrose, 25 mM Tris-HCl pH 8.0, 50 mM EDTA) plus lysozyme (5 mg/ml) and incubated at 37° for 15 minutes. Then, 0.1 ml of 10 mg/ml Proteinase K (prepared fresh in lysis buffer) was added, along with 1.0 ml of 10% sodium dodecyl sulfate (SDS). This mixture was immediately incubated at 70° C. for 15 minutes and then cooled on ice. Next, 2.5 ml of 5 M potassium acetate was added and mixed by gentle inversion before placing on ice for 15 minutes. After gently extracting the material with TE saturated phenol, the layers were separated by centrifugation (10,000 rpm for 10 minutes) and the aqueous phase was transferred to a fresh tube using a pipet with the tip broken off. After gently extracting the material with an equal volume of Sevag, the layers were again separated, the aqueous phase transferred to a fresh tube and the DNA precipitated with ethanol (two volumes) at room temperature. The precipitate was washed with 70% ethanol and then dissolved in 5 ml of TE. RNase A (final concentration of 50 μg/ml) and RNase T1 (final concentration of 1 μg/ml) were added and this solution was incubated at 37° C. for 30 minutes. After extracting twice with phenol, twice with Sevag and then precipitating with ethanol (two volumes), the DNA was dried in vacuo and redissolved in TE (around 1 ml for a 50 ml culture). The DNA was sized on a 0.3% agarose gel and was found to have an average size of 70 kb.

Next, 200 μg of *Streptomyces ambofaciens* chromosomal DNA were incubated with 85 units of MboI in a 1,000 μl reaction at 37° C. for three minutes. This particular condition was found, empirically, to give the desired suitable distribution of partially digested DNA. The DNA was extracted with phenol, Sevag, and precipitated with ethanol (1/10 volume of 3M NaOAc, three volumes ethanol at −70° C. for 30 minutes). The precipitate was collected by centrifugation (15 minutes) in an Eppendorf centrifuge and then the DNA was dissolved in 125 μl of water. After saving ~5 μg of DNA for use in determining whether the subsequently performed dephosphorylation was complete, the rest of the DNA was added to 20 μl of 10X bacterial alkaline phosphase (BAP) buffer and 80 μl (24 units/ml) of BAP. This mixture was incubated at 70° C. for one hour and then 80 μl of BAP was added and incubated for an additional hour. The DNA was extracted with phenol, Sevag, precipitated as taught directly above, and dissolved in 50 μl TE. The size of this DNA was estimated on a 0.3% agarose gel and was found to be ~30 kb.

C. Ligation of the Vector DNA to the Insert DNA

About 2 μl (approximately 1 μg) of vector pKC505 DNA that was HpaI-digested, dephosphorylated and BamHI-digested along with 4 μl (approximately 1.2 μg) of donor DNA MboI partials that have been dephosphorylated ligated in a 10 μl reaction with 400 units of T4 DNA ligase for 16 hours at 16° C. The ligation was monitored by running 5 μl of the ligation reaction mixture, along with unligated DNA controls, on a 0.3% agarose gel.

D. In Vitro Packaging

Packaging was performed by adding about 2.5 μl of the ligation mixture to the Gigapack* freeze-thaw extract (10 μl)-containing tube. To this, 15 μl of the Sonic extract was added, the solution was gently mixed, centrifuged briefly and then incubated for two hours at room temperature (24° C.). To this mixture, about 0.5 ml of SM (100 mM NaCl, 10 mM MgSO4, 50 mM Tris-HCl pH 7.5, 0.02% gelatin) and 25 μl of chloroform were added, mixed and centrifuged for one minute in an Eppendorf centrifuge to clarify. Chloroform was added to kill any living bacteria. The supernatant was used to infect *E. coli* cells.

* Packaging kits are available from several manufacturers.
 Gigapack Vector Cloning Systems, 3770 Tansy Street, San Diego, Calif. 92121
 Promega Biotec, 2800 S. Fish Hatchery Road, Madison, Wis. 53711

E. Transduction of *E. coli* K12 SF8

*E. coli* K12 SF8 (NRRL B-15835) was inoculated into 5 ml of Tryptone yeast extract supplemented with 0.2% maltose and 10 mM magnesium sulfate (TYMM). The culture was incubated overnight at 37° C. without aeration. After 50 ml more TYMM were added to the overnight culture, the culture was incubated three hours at 37° C. without aeration. The cells were centrifuged at 6,000 rpm for five minutes and the pellet resuspended in three ml of TM (10 mM Tris-HCl pH 7.6, 10 mM MgSO4).

About 0.2 ml each of the cells were infected with 10 μl or 50 μl of the in vitro packaged phage. Adsorption was done for 10 minutes at 37° C. Upon the addition of 1 ml of TY broth, the mixtures were incubated for two hours at 30° C. (All *E. coli* cultures carrying pKC505 or its derivatives are grown at 30°–34° C. rather than at 37°–42° C.). Aliquots (0.1 ml) were plated on TY plates supplemented with 100 μg/ml apramycin and incubated overnight at 30° C. The success of the cloning experiment was demonstrated by the presence of 27 transductants/0.1 ml for the 10 μl packaged lysate and 130 transductants/0.1 ml for the 50 μl packaged lysate.

Having shown that the packaged DNA is good in transduction, a scaled-up reaction was performed with the remaining phage lysate. Thus, ~500 μl of phage lysate was added to 1.5 ml of TM in a 50 ml Erlenmeyer flask and shaken for 15 minutes at 30° C. to evaporate any remaining chloroform. The SF8 cells were prepared as taught above except that the pellet was resuspended in 0.5 ml TM. These cells were added to the phage and incubated at 37° C. for 10 minutes without shaking. Ten ml of TY broth were added and the cells were incubated at 30° C. for 90 minutes with shaking. After centrifugation (6,000 rpm for five minutes) the cells were resuspended in three ml of TM and plated (0.1 ml/plate) on 30 TY plates supplemented with apraymycin. The plates were incubated overnight at 30° C. Approximately 1,000 colonies/plate were obtained for a total of 30,000 colonies. The *E. coli* transformants were pooled to create a primary library, from which a primary plasmid pool was made.

F. Transformation of *Streptomyces griseofuscus*

From a fully grown overnight culture of *S. griseofuscus* (ATCC 23916) about 0.5 ml was used to inoculate 10 ml of TSB plus 0.5% glycine. After incubation at 34° C. for 24 hours, the culture was homogenized using a tissue grinder and 0.5 ml of this homogenate was used to inoculate a new 10 ml TSB with 0.5% glycine culture. This culture was also incubated at 34° C. for 24 hours. At this point the cells can be stored frozen at −70° C.

The culture was transferred to a fifteen ml sterile polystyrene centrifuge tube and spun at 5,000 rpm for 10 minutes. The recovered pellet was washed once with 10 ml of P medium and then repelleted. The pellet was washed with 10 ml of P medium with 1 mg/ml lysozyme and incubated at 30° C. for ½ hour. Protoplast formation can be monitored by taking small samples for observation under a phase contrast microscope to identify a sample containing spherical cells. The protoplasts were centrifuged as taught above and washed twice in P media. The final pellet was resuspended in 2 ml of P medium.

About 150 μl of protoplasts in an 1.5 ml Eppendorf tube were added to 2 μl of the primary plasmid pool DNA and gently mixed. Immediately, 100 μl of 50% polyethylene glycol (MW 1000 in P Medium) were added and allowed to sit for two minutes. Next, 100 μl of the transformation mix in 4 ml of R2 top agar were plated on dried R2 plates. These plates were incubated at 30° C. for 20 hours. After overlaying with R2 top agar containing enough apramycin to give a final concentration of 25 μg/ml, the plates were incubated at 30° C. Transformants appeared two to three days after the overlay. A total of about 10,000 apraymycin resistant colonies were obtained.

These colonies were scraped, pooled and grown in TSB overnight at 30° C. The overnight broth culture was diluted (5% inoculum) in TSB supplemented with spiramycin (25 μg/ml) and the culture was incubated for about three days by which time the culture had reached early stationary phase. Rapid plasmid minipreps were made from these cells in substantial accordance with the teaching of Kieser, 1984, *Plasmid* 12:19 and they were used to transform *E. coli* DH1 cells. Apramycin resistant colonies were selected and twelve clones were analyzed for their plasmid DNA by restriction enzyme analysis. Of these clones, eleven were of one kind with an ~20 kb insert; the twelfth one was too small. One of the eleven clones was designated pKC514.

EXAMPLE 7

Screening of the Genomic Library by Colony Hybridization

Approximately 5,000 independent *E. coli* colonies of the primary genomic library were screened according to conventional published procedures using a nick-translated [$^{32}$P]-labeled BamHI insert from pKC514 as a probe. The prehybridization, hybridization, and wash conditions were performed in accordance with the teaching of Maniatis et al., *Molecular Cloning: A Laboratory Manual,* Cold Spring Harbor Laboratory, 1982. Positive colonies were identified by autoradiography. One of the clones had a plasmid, designated pKC570, whose structure was very similar to that of pKC514. Plasmid pKC570 transforms *S. griseofuscus* cells to spiramycin resistance.

EXAMPLE 8

Culture of *E. coli* K12 C600R$_k$-M$_k$-/pHJL225 and Isolation of Plasmid DNA

Figure 6:
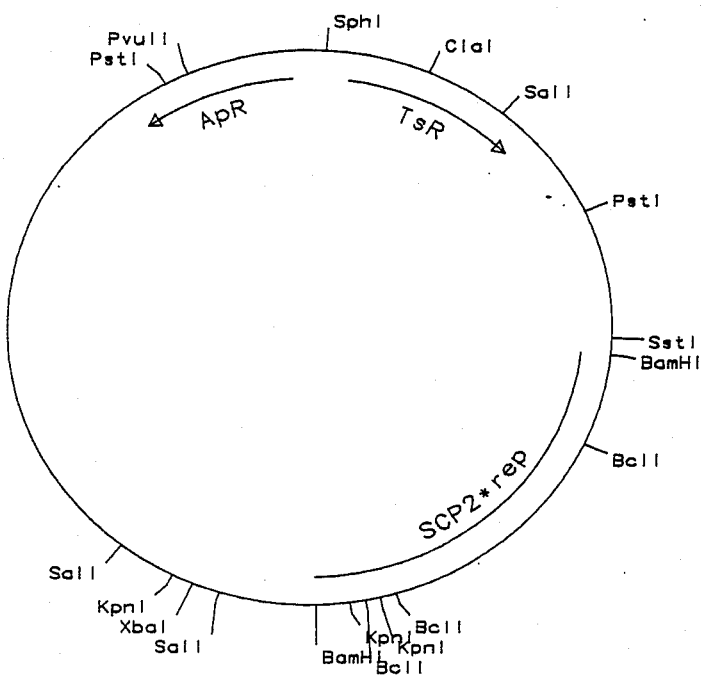
FIG. 6 shows the restriction site and function map of plasmid pHJL225.

The desired culture and subsequent isolation of plasmid pHJL225 was carried out in substantial accordance with the teaching of Example 1. The strain *E. coli* K12 C600R$_k$-M$_k$-/pHJL225 is available to the public, as a preferred source and stock reservoir of the plasmid, under the accession number NRRL B-18052. A restriction site and function map of plasmid pHJL225 is presented in FIG. 6 of the accompanying drawings.

EXAMPLE 9

Construction of Moderate Copy Number Plasmids pHJL400 and pHJL401

A. NdeI Digestion of Plasmid pUC19

About 1 μg of plasmid pUC19 (Pharmacia, Inc., 800 Centennial Dr., Piscataway, N.J.) was digested to completion with NdeI restriction enzyme to generate linear vector fragments which were treated with calf intestinal alkaline phosphatase.

B. Construction of Intermediate Plasmid pHJL399

About 35 μl (17.5 μg) of plasmid pHJL225 (isolated in Example 8) were digested with BamHI restriction enzyme to completion and the desired ~2.2 kb BamHI fragment containing the SCP2* replicon was purified by AGE. Next, an 1.1 kb BclI fragment from plasmid pIJ702 (ATCC 39155) comprising the thiostrepton resistance-conferring gene was isolated according to conventional and well understood techniques. These fragments were ligated together to construct plasmid pHJL399.

Thiostrepton selected *S. lividans* TK23 transformants containing pHJL399. The transformants were analyzed by restriction enzyme analysis and the plasmid pHJL399 DNA was isolated for use in the construction of plasmids pHJL400 and 401.

C. NdeI Digestion of Plasmid pHJL399 and Ligation of Fragments

Figure 7:
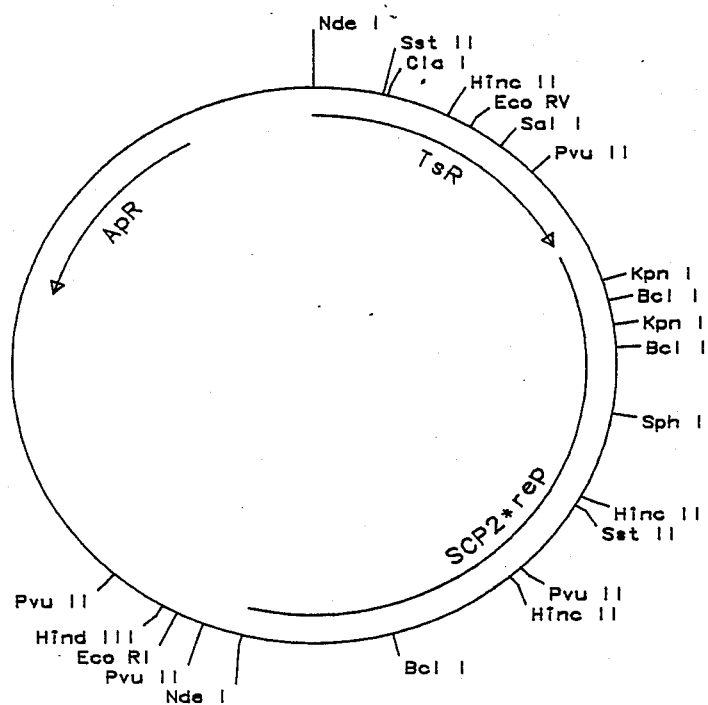
FIG. 7 shows the restriction site and function map of plasmid pHJL401.

About 30 μl (1 μg) of plasmid pHJL399 were digested with NdeI restriction enzyme to completion. Since there is a unique NdeI site in plasmid pHJL399, a single, linear fragment was generated. T4 DNA ligase joined the pHJL399 NdeI fragment to NdeI-digested pUC19. A diagram of plasmid pHJL401 construction is presented in FIG. 7 of the accompanying drawings.

D. Transformation of *E. coli* JM109

*E. coli* JM109 cells (Janisch-Perron et al., 1985, *Gene* 33:103) were made competent and transformed with the above ligation mix using the calcium chloride/rubidium chloride procedure essentially as described in Maniatis et al., 1982. Transformants were identified by resistance to ampicillin and formation of blue colonies on media containing X-gal and verified by restriction digests of plasmid DNA. Plasmids pHJL400 and pHJL401 differ only in the orientation of the NdeI restriction fragment of plasmid pHJL399. Both plasmids transform *S. griseofuscus* and *S. lividans* to thiostrepton resistance.

EXAMPLE 10

Construction of Plasmids pKC549 and pKC550

Plasmid pKC514 was digested with Sau3AI restriction enzyme to generate partially cut DNA. This was ligated to BamHI-cut pHJL401 and the ligation was used to transform *E. coli* JM109 cells selecting for Ap$^R$. Greater than 50% of the clones appeared to have inserts. All the transformants were pooled to make plasmid DNA. The pooled plasmid DNA was transformed into *S. griseofuscus* selecting for thiostrepton resistance. These transformants were pooled and grown in TSB supplemented with 25 μg/ml of spiramycin. After the culture had grown, the cells were plated on TSA plates with 25 μg/ml thiostrepton and plasmid DNA was made from spriamycin-resistant colonies that came up on the plate. This plasmid DNA was used to transform *E. coli* JM109 with selection for Ap$^R$ phenotypes. White colonies were picked and the plasmid DNA was analyzed. All of the six clones analyzed had the same plasmid and one of these, designated pKC550, was transformed into *S. griseofuscus* selecting for thiostrepton resistance. The resulting transformants were resistant to spiramycin. This subcloning experiment indicates that the spiramycin resistance-conferring gene of the present invention has been localized within an ~3.4 kb Sau3AI restriction fragment of cosmid pKC550.

Plasmid pKC514 was digested with SalI to generate partially cut DNA. This was ligated to SalI-cut pHJL401. The ligation mixture was used, as described above for pKC550, to isolate pKC549, which also conferred spiramycin resistance. Both of the plasmids were mapped by restriction enzyme digests and by DNA blotting. Plasmids pKC549 and pKC550 are illustrated in FIGS. 4 and 5 of the accompanying drawings.

I claim:

1. A Streptomyces-functional recombinant DNA expression vector which comprises a spiramycin resistance-conferring sequence of *Streptomyces ambofaciens* DNA that is encoded on plasmid pKC550.

2. The vector pKC550.

3. The vector of claim 1 which is pKC514.

4. The vector of claim 1 which is pKC549.

5. The spiramycin resistance-conferring sequence of claim 1.

6. A spiramycin-sensitive, restrictionless host cell transformed by the vector of claim 1, said host cell selected from the group consisting of restrictionless Streptomyces, Nocardia, and *E. coli* species.

7. The transformed host cell of claim 6 which is Streptomyces.

8. The transformed host cell of claim 6 which is *E. coli*.

9. The transformed host cell of claim 6 which is Nocardia.

10. The transformed host cell of claim 7 which is *Streptomyces griseofuscus*/pKC550.

11. The transformed host cell of claim 7 which is *Streptomyces griseofuscus*/pKC514.

12. The transformed host cell of claim 7 which is *Streptomyces griseofuscus*/pKC549.

13. The transformed host cell of claim 8 which is *E. coli* JM109/pKC550.

14. The transformed host cell of claim 8 which is *E. coli* DH1/pKC514.

* * * * *